(12) United States Patent
Brown et al.

(10) Patent No.: US 6,784,181 B2
(45) Date of Patent: Aug. 31, 2004

(54) PIPERAZINE-CONTAINING COMPOUNDS USEFUL IN THE TREATMENT OF PAIN

(75) Inventors: William Brown, St. Laurent (CA); Christopher Walpole, St. Laurent (CA); Niklas Plobeck, St. Laurent (CA)

(73) Assignee: AstraZeneca AB, Sodertalje (SE)

( * ) Notice: Subject to any disclaimer, the term of this patent is extended or adjusted under 35 U.S.C. 154(b) by 53 days.

(21) Appl. No.: 10/149,911

(22) PCT Filed: Dec. 15, 2000

(86) PCT No.: PCT/SE00/02559

§ 371 (c)(1),
(2), (4) Date: Oct. 21, 2002

(87) PCT Pub. No.: WO01/45637

PCT Pub. Date: Jun. 28, 2001

(65) Prior Publication Data

US 2003/0119845 A1 Jun. 26, 2003

(30) Foreign Application Priority Data

Dec. 20, 1999 (SE) .............................................. 9904673

(51) Int. Cl.⁷ .................... A61K 31/496; C07D 401/06; C07D 401/14; C07D 405/14; C07D 409/14

(52) U.S. Cl. .................................. 514/253.06; 544/363

(58) Field of Search ...................... 544/363; 514/253.06

(56) References Cited

U.S. PATENT DOCUMENTS

| | | | |
|---|---|---|---|
| 3,940,386 A | 2/1976 | Szabo et al. ................. | 260/240 |
| 5,574,159 A | 11/1996 | Chang et al. ................. | 544/396 |
| 5,681,830 A | 10/1997 | Chang et al. ................. | 514/85 |
| 5,807,858 A | 9/1998 | Chang et al. ................. | 514/255 |
| 6,130,222 A | 10/2000 | Roberts et al. ........ | 514/255.04 |

FOREIGN PATENT DOCUMENTS

| | | |
|---|---|---|
| DE | 24 31 178 | 1/1975 |
| DE | 29 00 810 | 7/1980 |
| EP | 0 133 323 | 2/1985 |
| EP | 0 166 302 | 1/1986 |
| EP | 0 283 310 | 9/1988 |
| EP | 0 289 227 | 11/1988 |
| FR | 2 696 744 | 4/1999 |
| GB | 2 076 403 | 12/1981 |
| GB | 2 210 366 | 6/1989 |
| JP | 7-138230 | 5/1995 |
| WO | WO 86/04584 | 8/1986 |
| WO | WO 91/07967 | 6/1991 |
| WO | WO 93/15062 | 8/1993 |
| WO | WO 95/04051 | 2/1995 |
| WO | WO/97/23466 | 7/1997 |
| WO | WO 98/28270 | 7/1998 |
| WO | WO 98/28275 | 7/1998 |
| WO | WO 99/33806 | 7/1999 |

OTHER PUBLICATIONS

Burkey et al., Medline Abstract for Life Sci., vol. 62,p1531–1536 (1998).*
Nagase et al. Medline Abstract for Life Sci., vol. 68,p. 2227–2231 (2001).*
Abstract for HU 217619. A corresponding English language PCT application is cited above as Reference AF1.
Abstract for HU 215847. A corresponding English language PCT application is cited above as Reference AG1.
Greene, "Protective Groups in Organic Synthesis," pp. 267–268 and 331 (1981).
Bilsky, et al., "Characterization of Enantiomers of (±)BW373U86 and Related Compounds: Highly Selective Non–Peptidic Delta Opioid Agonists," *Reg. Peptides* 54:25–26 (1994).
Bilsky, et al., "SNC 80, A Selective, Nonpeptidic and Systemically Active Opioid Delta Agonist," *J. Pharmacol. Exper. Therap.* 273:359–366 (1995).
Calderon, et al., "Probes for Narcotic Receptor Mediated Phenomena. 19. Synthesis of (+)-4-[(αR)-α-((2S, 5R)-4-Allyl-2, 5-Dimethyl-1-Piperazinyl)-3-Methoxybenzyl]-N,N-Diethylbenzamide (SNC 80): A Highly Selective, Nonpeptide o Opioid Receptor Agonist," *J. Med. Chem.* 37:2125–2128 (1994).

(List continued on next page.)

*Primary Examiner*—Emily Bernhardt
(74) *Attorney, Agent, or Firm*—Michael A. Sanzo; Fitch, Even, Tabin & Flannery

(57) ABSTRACT

The present invention is directed to a compound of general formula (I),

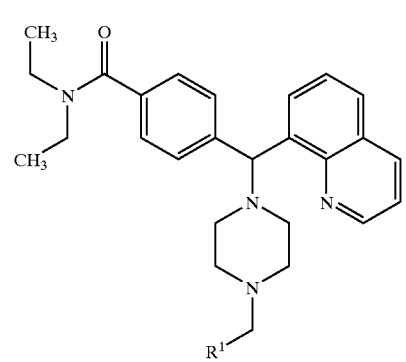

wherein R¹ is selected from phenyl, pyridinyl, thiophenyl, furanyl, imidazolyl; each phenyl ring and heteroaromatic ring optionally and independently being further substituted by 1, 2 or 3 substituents selected from straight and branched $C_1$–$C_6$ alkyl, $NO_2$, $CF_3$, $C_1$–$C_6$ alkoxy, chloro, fluoro, bromo, and iodo, as well as their pharmaceutically acceptable salts. The invention includes pharmaceutical compositions comprising these compounds and the use of the compounds in therapy, in particular in the management of pain.

22 Claims, No Drawings

OTHER PUBLICATIONS

Calderon, et al., "Probes for Narcotic Receptor Mediated Phenomena. 23. Synthesis, Opioid Receptor Binding, and Bioassay of the Highly Selective o Agonist (+)-4-[(αR)-α-((2S,5R)-4-Allyl-2,5-Dimethy-1-Piperazinyl)-3-Methoxybenzyl]-N,N-Diethylbenzamide (SNC 80) and Related Novel Nonpeptide o Opioid Receptor Ligands," *J. Med. Chem.* 40:695-704 (1997).

Chang, et al., "A Novel, Potent and Selective Nonpeptide *Delta* Opioid Receptor Agonist BW373U86," *J. Pharmacol. Exper. Therap.* 267:852-857 (1993).

Katrizky, et al., "Benzotriazole-Mediated Arylalkylation and Heteroarylalkylation," *Chem. Soc. Rev.* 23:363-442 (1994).

Kingsbury, et al., "Synthesis of Structural Analogs of Leukotriene B, and Their Receptor Binding Activity," *J. Med. Chem.* 36:3308-3320 (1993).

Lopez, et al., "Exploring the Structure-Activity Relationships of [1-(4-teri-Butyl-3'-Hydroxy)Benzhydryl-4-Benzylpiperzine] (SL-3111), a High-Affinity and Selective o-Opioid Receptor Nonpeptide Agonist Ligand," *J. Med. Chem.* 42:5359-5368 (1999).

Plobeck, et al., "New Diarylmethylpiperazines as Potent and Selective Nonpeptide o Opioid Receptor Agonists with Increased *In Vitro* Metabolic Stability," *J. Med. Chem.* 43:3878-3894 (2000).

Suggs, et al., "Facile Synthesis of 8-Substituted Quinolines," *J. Org. Chem.* 45:1514-1515 (1980).

Takemori, et al., "Selective Natrexone-Derived Opioid Receptor Antagonists," *Annu. Rev. Pharmacol. Toxicol.* 32:239-269 (1992).

Zhang, et al., Probes for Narcotic Receptor Mediated Phenomena. 26. Synthesis and Biological Evaluation of Diarylmethylpiperazines and Diarylmethylpiperdines as Novel, Nonpeptidic o Opioid Receptor Ligands, *J. Med. Chem.* 42:5455-5463 (1999).

Dialog Abstract for FR 2696744 (Apr. 15, 1994).

Dialog Abstract for DE 2431178 (Jan. 16, 1975).

Dialog abstract for Reference DE 2900 810 (Jul. 24, 1980).

Dialog abstract for JP 7-138230 (May 30, 1995).

Chemical Abstract No. 8843b for JP 7-138230 (May 30, 1995), (1996).

\* cited by examiner

PIPERAZINE-CONTAINING COMPOUNDS USEFUL IN THE TREATMENT OF PAIN

CROSS REFERENCE TO RELATED APPLICATIONS

The present application represents U.S. national stage of international application PCT/SE00/02559, which had an international filing date of Dec. 15, 2000, and which was published in English under PCT Article 21(2) on Jun. 28, 2001.

The international application claims priority to Swedish application 9904673-2. filed on Dec. 20, 1999.

FIELD OF THE INVENTION

The present invention is directed to novel compounds, to a process for their preparation, their use and pharmaceutical compositions comprising the novel compounds. The novel compounds are useful in therapy, and in particular for the treatment of pain.

BACKGROUND AND PRIOR ART

The δ receptor has been identified as having a role in many bodily functions such as circulatory and pain systems. Ligands for the δ receptor may therefore find potential use as analgesics, and/or as antihypertensive agents. Ligands for the δ receptor have also been shown to possess immuno-modulatory activities.

The identification of at least three different populations of opioid receptors ($\mu$, δ and κ) is now well established and all three are apparent in both central and peripheral nervous systems of many species including man. Analgesia has been observed in various animal models when one or more of these receptors has been activated.

With few exceptions, currently available selective opioid δ ligands are peptidic in nature and are unsuitable for administration by systemic routes. One example of a non-peptidic δ-agonist is SNC80 (Bilsky E. J. et al., *Journal of Pharmacology and Experimental Therapeutics*, 273(1), pp. 359–366 (1995)). There is however still a need for selective δ-agonists having not only improved selectivity, but also an improved side-effect profile.

Thus, the problem underlying the present invention was to find new analgesics having improved analgesic effects, but also with an improved side-effect profile over current $\mu$ agonists, as well as having improved systemic efficacy.

Analgesics that have been identified and are existing in the prior art have many disadvantages in that they suffer from poor pharmacokinetics and are not analgesic when administered by systemic routes. Also, it has been documented that preferred δ agonist compounds, described within the prior art, show significant convulsive effects when administered systemically.

We have now found that certain compounds not specifically disclosed by, but included within the scope of WO 98/28270, exhibit surprisingly improved δ-agonist properties and in vivo potency relative to compounds disclosed in WO98/28270, when administered systemically. The compounds of the present invention exhibit significant and unexpected increased levels of delta receptor agonism and metabolic stability.

Outline of the Invention

The novel compounds according to the present invention are defined by the formula I

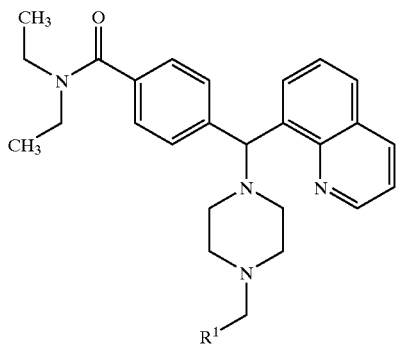

wherein
$R^1$ is selected from
(i) phenyl;

(ii) pyridinyl

(iii) thiophenyl
(iv) furanyl

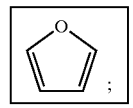

(v) imidazolyl

(vi) triazolyl
where each $R^1$ phenyl ring and $R^1$ heteroaromatic ring may optionally and independently be further substituted by 1, 2 or 3 substituents selected from straight and branched $C_1$–$C_6$ alkyl, $NO_2$, $CF_3$, $C_1$–$C_6$ alkoxy, chloro, fluoro, bromo, and iodo. The substitutions on the phenyl ring and on the heteroaromatic ring may take place in any position on said ring systems.

Within the scope of the invention are also pharmaceutically acceptable salts of the compounds of the formula I, as well as isomers thereof.

In a preferred embodiment of the invention, the compounds of formula I are present as the (+)-enantiomer, or as the (−)-enantiomer.

By "isomers" we mean compounds of the formula I, which differ by the position of their functional group and/or orientation. By "orientation" we mean stereoisomers, diastereoisomers, regioisomers and enantiomers.

The novel compounds of the present invention are useful in therapy, especially for the treatment of various pain conditions such as chronic pain, neuropathic pain, acute pain, cancer pain, pain caused by rheumatoid arthritis, migraine, visceral pain etc. This list should however not be interpreted as exhaustive.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of opioid receptors is present or implicated in that paradigm. This may involve the use of isotopically labelled versions of the compounds of the invention in diagnostic techniques and imaging applications such as positron emission tomography (PET).

Compounds of the invention are useful for the treatment of diarrhoea, depression, anxiety, urinary incontinence, various mental illnesses, cough, lung oedema, various gastrointestinal disorders, spinal injury and drug addiction, including the treatment of alcohol, nicotine, opioid and other drug abuse and for disorders of the sympathetic nervous system for example hypertension. Compounds of the invention are useful as an analgesic agent for use during general anaesthesia and monitored anaesthesia care. Combinations of agents with different properties are often used to achieve a balance of effects needed to maintain the anaesthetic state (eg. amnesia, analgesia, muscle relaxation and sedation). Included in this combination are inhaled anaesthetics, hypnotica, anxiolytics, neuromuscular blockers and opioids.

Also within the scope of the invention is the use of any of the compounds according to the formula I above, for the manufacture of a medicament for the treatment of any of the conditions discussed above.

A further aspect of the invention is a method for the treatment of a subject suffering from any of the conditions discussed above, whereby an effective amount of a compound according to the formula I above, is administered to a patient in need of such treatment. Also included within the scope of the present invention, is any novel intermediate as described in Scheme I hereinafter useful in the synthesis of compounds of formula I above.

Methods of Preparation

The compounds according to the present invention may be prepared by following any one of the procedures described in Schemes I, II, III, and IV. These known procedures are described in *J. March, Advanced Organic Chemistry*, 4$^{th}$ Edition, John Wiley and sons (1992); Katritsky, A. R., Lan, X. *Chem. Soc. Rev.*, pp. 363–373 (1994), which are hereby incorporated by reference.

SCHEME I

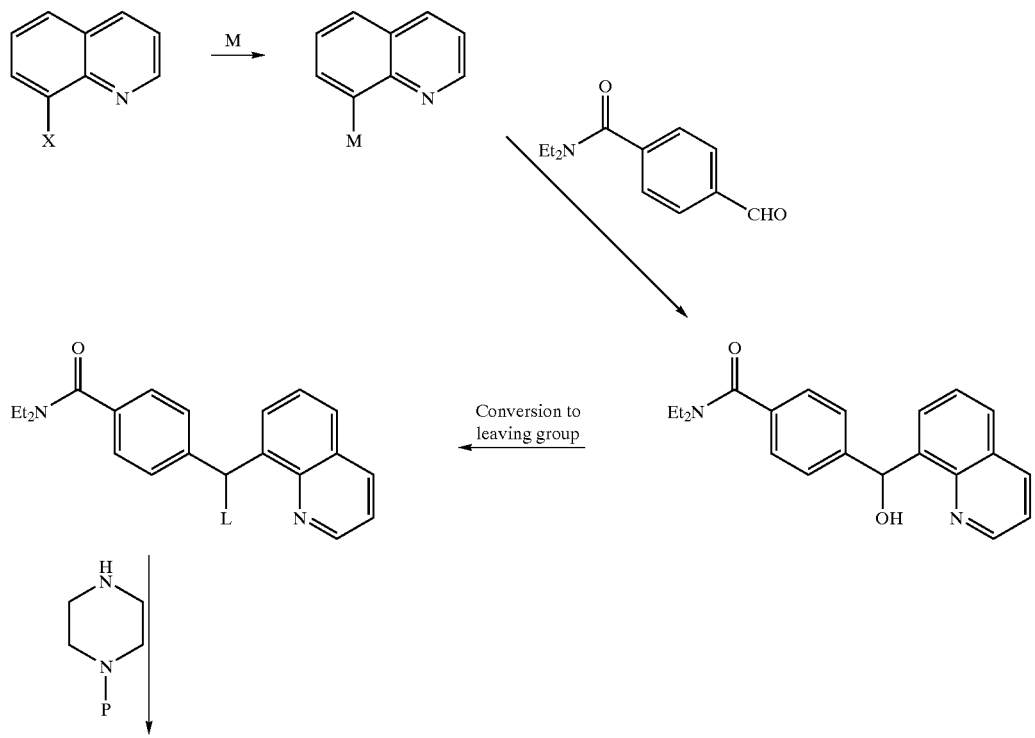

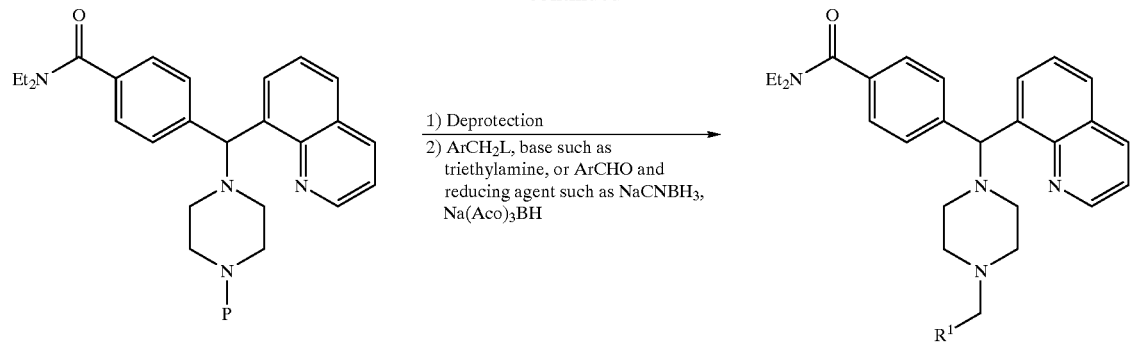
P=a protecting group such as Bn, Boc, CBz
M=Li, Mg, Zn
X=Br, I
L=Cl, Br, OMs, OTs, I
R¹=as defined in formula (I) above
SCHEME II
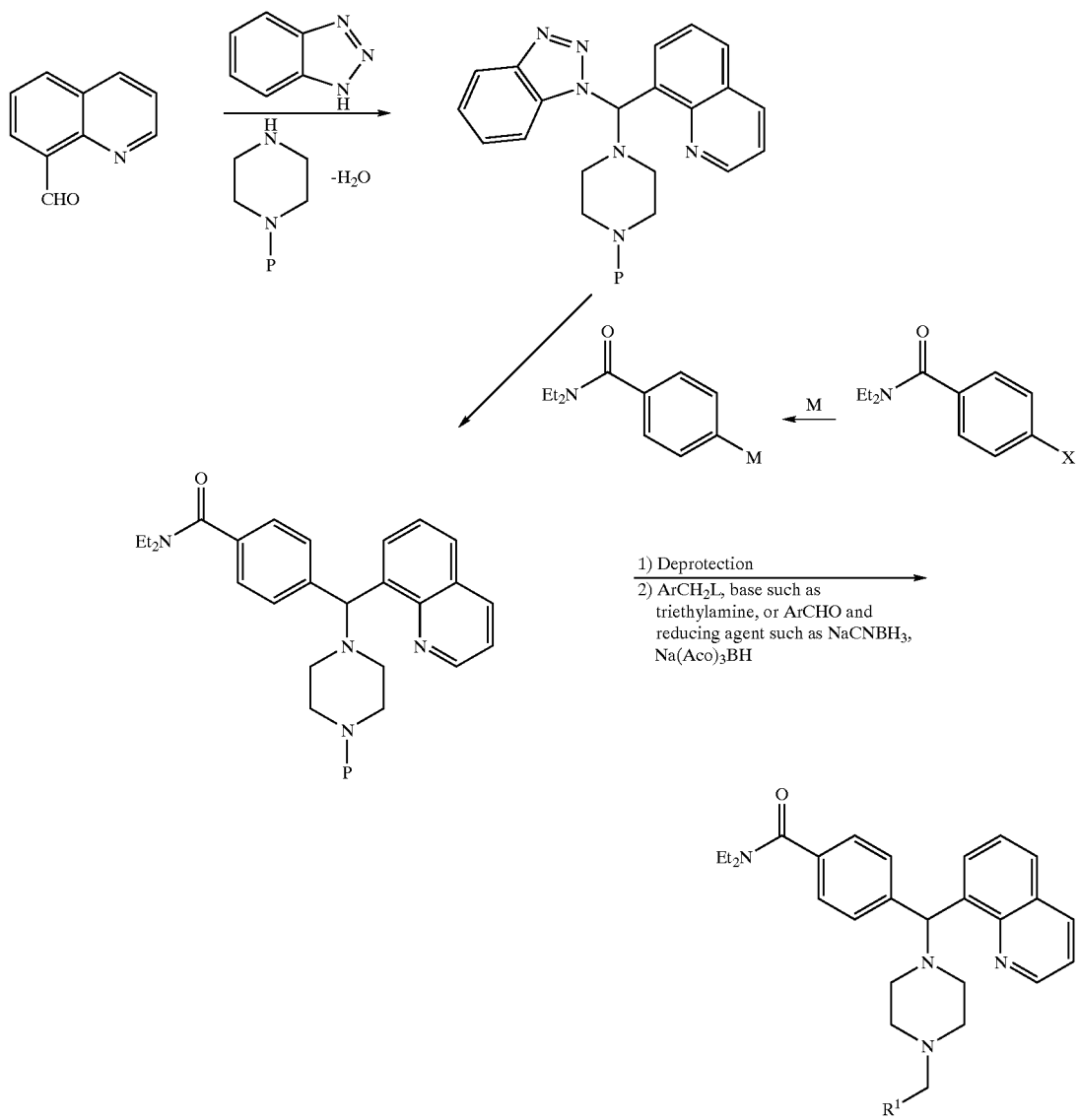

P=a protecting group such as Bn, Boc, CBz
M=Li, Mg, Zn
X=Br, I
L=Cl, Br, OMs, OTs, I
R¹=as defined in formula (I) above
M=Li, Mg, Zn
X=Br, I
L=Cl, Br, OMs, OTs, I
R¹=as defined in formula (I) above
SCHEME III
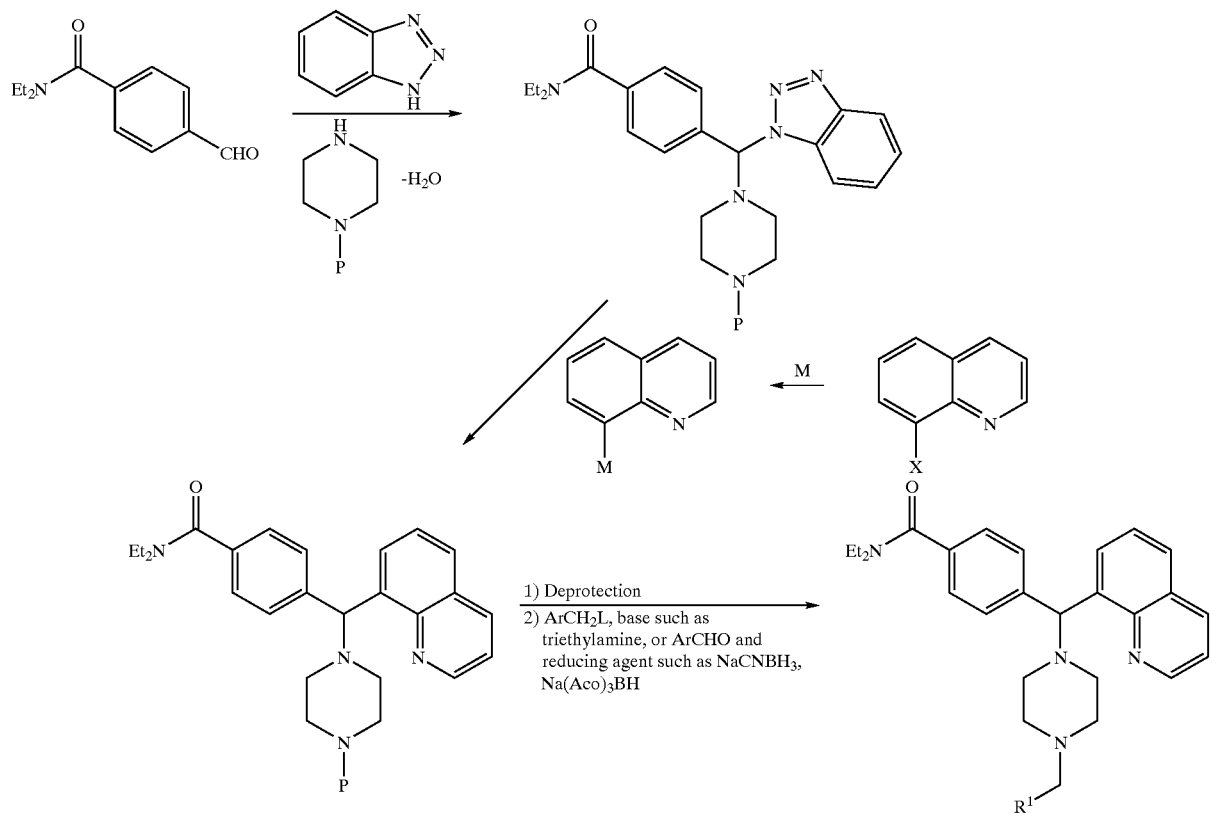
P=a protecting group such as Bn, Boc, CBz
SCHEME IV
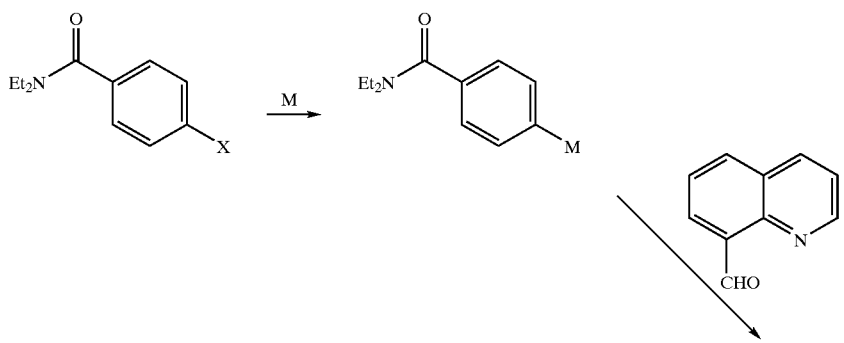

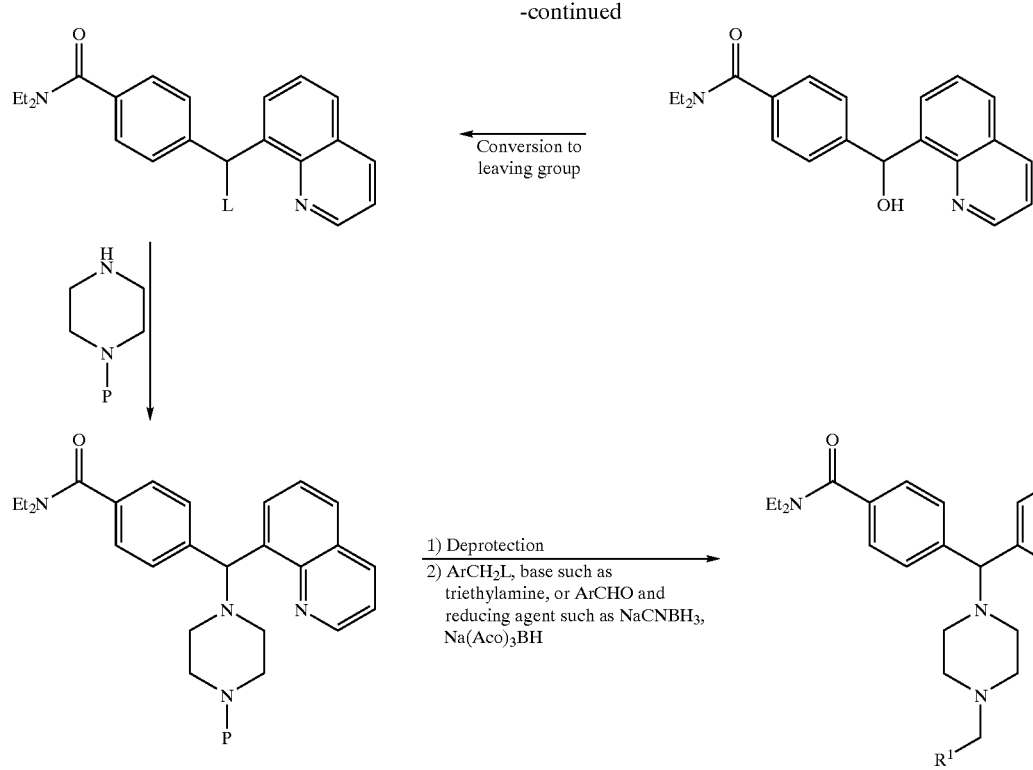

P=a protecting group such as Bn, Boc, CBz
M=Li, Mg, Zn
X=Br, I
L=Cl, Br, OMs, OTs, I
$R^1$=as defined in formula (I) above

EXAMPLES

The invention will now be described in more detail by the following Examples, which are not to be construed as limiting the invention.

Example 1

Preparation of 4-[(4-benzyl-1-piperazinyl)(8-quinolinyl)methyl]-N,N-diethylbenzamide dihydrochloride (Compound 2)

The title compound 2 was prepared by following the synthetic procedure of Scheme 1 below.

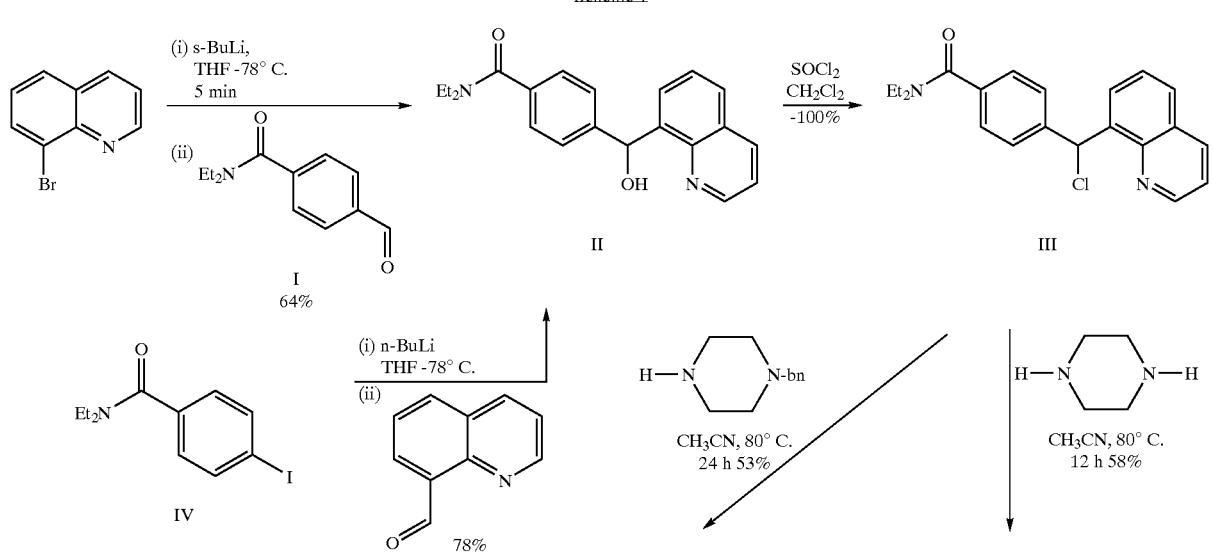

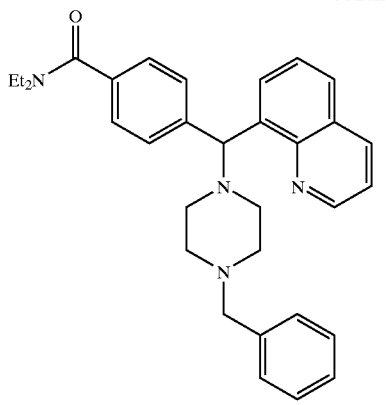

Compound 2

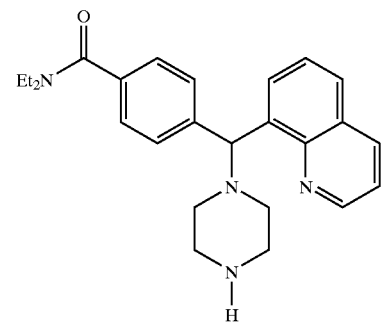

Compound 1

(i) Preparation of N,N-diethyl-4-formylbenzamide (Compound I).

4-Formylbenzoic acid (11.2 g, 74.6 mmol) and triethylamine (10.4 mL, 75 mmol) was dissolved in THF (100 mL) and cooled to −10° C. i-Butylchloroformate (10.3 mL, 78 mmol) was added and stirring was continued for 10 minutes at −10° C. before diethylamine (9.7 mL, 94 mmol) was added and solution was allowed to reach 25° C. After concentration, aqueous workup and chromatography on silica (0–100% EtOAc in heptane), a total of 7.4 g (50%) compound I was obtained.

(ii) Preparation of N,N-diethyl-4-[hydroxy(8-quinolinyl)methyl]benzamide (Compound II)

8-Bromoquinoline (3.0 g, 14.4 mmol) was dissolved in dry THF (150 mL) and cooled to −78° C. under nitrogen. s-BuLi (11.1 mL, 1.3 M in pentane, 14.4 mmol) was added dropwise during 5 min (Preparation and reactions with 8-lithioquinoline: Suggs, *J. Org. Chem.* 1980, 45, 1514.). After further 5 min, N,N-diethyl-4-formylbenzamide (3.5 g, 17.0 mmol) was added dissolved in THF (5 mL). The solution was stirred 1 h, then $NH_4Cl$ (aq.) was added. After concentration, aqueous workup and chromatography on silica (0–100% EtOAc in heptane), a total of 3.5 g (70%) compound II was obtained. MS: 334, 262, 234, 215, 204, 178, 156, 129.

Alternative Route to Prepare Compound II From N,N-diethyl-4-iodobenzamide (Compound IV)

Compound IV (0.67 g, 2.2 mmol) was dissolved in dry THF (25 mL) and cooled to −78° C. under nitrogen. n-BuLi (1.3 mL, 1.6 M in hexane, 2.2 mmol) was added dropwise during 5 min. After further 10 min, 8-formylquinoline (0.17 g, 1.1 mmol) (8-formylquinoline was made from 8-methylquinoline by oxidation with selenium dioxide at 150–155° C. for 12 h (Kingsbury, *J. Med. Chem.* 1993, 3308.) was added dissolved in THE (1 mL). The solution was stirred 1 h, then $NH_4Cl$ (aq.) was added. After concentration, aqueous workup and chromatography on silica (0–100% EtOAc in heptane), a total of 0.29 g (78%) compound II was obtained.

(iii) Preparation of 4-[chloro(8-quinolinyl)methyl]-N,N-diethylbenzamide (Compound III).

Compound II (2.0 g, 6.6 mmol) was dissolved in dry $CH_2Cl_2$ (25 mL) and $SOCl_2$ (0.53 mL, 7.3 mmol) was added. The solution was stirred at 25° C. for 30 min and the solvent was evaporated in vacuo. Compound III was obtained as an oil (~100%) and used in the next reaction without further purification.

MS: 348, 333, 233, 215, 204, 156.

(iv) Preparation of N,N-diethyl-4-[1-piperazinyl(8-quinolinyl)methyl]benzamide (Compound 1).

The crude product compound III (~6.6 mmol) and piperazine (2.3 g, 26 mmol) was dissolved in dry MeCN (50 mL) and heated at reflux 12 h. The solvent was removed in vacuo, the residue dissolved in $CH_2Cl_2$ and washed with water and the organic phase dried ($K_2CO_3$) and evaporated in vacuo. After chromatography on silica (0–20% MeOH in $CH_2Cl_2$, 1% $NH_4OH$), a total of 1.8 g (68%, 2 steps) compound 1 was obtained. Further purification could be achieved by reverse phase chromatograpy (LiChroprep RP-18, 10–50% MeCN in water, 0.1% TFA) to give 1.2 g colorless product. The dihydrochloride salt was made by treatment with 2 eq. HCl in ether.

Mp: 180–90° C.

IR (KBr, $v_{max}$) 3297, 2982, 2716, 2474, 1611, 1434, 1380, 1288, 1098 $cm^{-1}$.

MS (amine): 402, 318, 246, 217, 109.

$^1$H NMR (amine, $CDCl_3$): δ 1.2, 1.1 (2s, 6H), 2.94, 2.51 (2m, 8H), 3.5–3.1 (m, 5H), 6.05 (s, 1H), 8.94–7.20 (m, 10H).

Anal. ($C_{25}H_{30}N_4O \times 3.2CF_3CO_2H$) C, N; H: calcd, 4.36; found, 3.90.

(v) Preparation of 4-[(4-benzyl-1-piperazinyl)(8-quinolinyl)methyl]-N,N-diethylbenzamide Dihydrochloride (the Title Compound 2)

Compound 1 (1.3 g, 3.2 mmol) and triethylamine (0.90 mL, 6.4 mmol) was dissolved in MeCN (10 mL). Benzyl bromide (0.77 mL, 6.4 mmol) was added with stirring at 25° C. After 4 h the solution was concentrated and purified by chromatography on silica (0–5% MeOH in $CH_2Cl_2$, or by reverse phase chromatograpy (LiChroprep RP-18, 20–80% MeCN in water, 0.1% TFA). A total of 2.2 g (72%) of the title compound 2 was obtained. Treatment with 2 eq. HCl (aq.) and freeze drying gave the dihydrochloride salt (3.6 g).

IR (2×HCl, KBr): 2388, 1606, 1434, 1356, 1287 ($cm^{-1}$).

$^1$H NMR (free amine, $CDCl_3$) δ=1.05 (m, 6H), 2.5 (m, 8H), 3.1–3.6 (m, 6H), 6.04 (s, 1H), 7.18–8.98 (m, 15H).

Anal. ($C_{32}H_{38}Cl_2N_4O$) C, H, N.

Alternative Procedure to Prepare the Title Compound 2 From Compound III

The crude product compound III (~13.2 mmol), triethylamine (2.0 mL, 14.5 mmol) and N-benzyl-piperazine (2.6 g, 14.5 mmol) was dissolved in dry MeCN (50 r) and heated at reflux 12 h. More N-benzyl-piperazine (0.5 g, 2.8 mmol) was added and heating continued for 12 h. The solvent was removed in vacuo, the residue dissolved in $CH_2Cl_2$ and washed with water and the organic phase dried ($K_2CO_3$) and evaporated in vacuo. After chromatography on silica (0–10% MeOH in $CH_2Cl_2$), a total of 3.5 g (53%) of the title compound 2 was obtained.

Examples 2 & 3

Separation of the Enantiomers of Compound 2 (Compounds 3 and 4)

The preparative separation of this compound was done on a Chiralcel OD column (50 mm×50 cm) using Hexane/EtOH/Diethylamine 85:15:0.1 as the mobile phase. On the Chiralcel OD column, the (+)-isomer was found to elute first.

Example 2

(−)4-[(4-benzyl-1-piperazinyl)(8-quinolinyl)methyl]-N,N-diethylbenzamide (Compound 3)

$[\alpha]_D^{25}$: −130° (c 0.78, MeOH)

$^1$H NMR: ($CD_3OD$): δ=1.05 (m, 6H), 3.0–3.6 (m, 14H), 5.90 (s, 1H), 7.22–8.20 (m, 13H), 8.78 (m, 1H), 9.50 (m, 1H).

ANALYSIS: Calc.w.3.1$H_2O$, C: 61.85, H: 7.17, N: 9.02, Found C: 61.84, H: 6.60, N: 8.89

Example 3

(+)4-[(4-benzyl-1-piperazinyl)(8-Quinolinyl)methyl]-N,N-diethylbenzamide (Compound 4)

$[\alpha]_D^{25}$: +130° (c 0.69, MeOH)

$^1$H NMR: ($CD_3OD$): δ=1.05 (m, 6H), 3.0–3.6 (m, 14H), 5.90 (s, 1H), 7.22–8.20 (m, 13H), 8.78 (m, 1H), 9.50 (m, 1H).

ANALYSIS: Calc.w.3.2$H_2O$, C: 61.67, H: 7.18, N: 8.99, Found C: 61.70, H: 6.46, N: 8.84

Example 4

Preparation of N,N-diethyl-4-[[4-(4-methylbenzyl)-1-piperazinyl](8-quinolinyl)methyl]benzamide (Compound 5)

The title compound 5 was prepared by following the synthetic procedure of Scheme 2 below.

Scheme 2

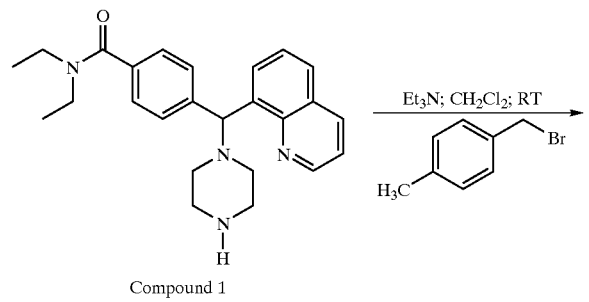

Compound 1

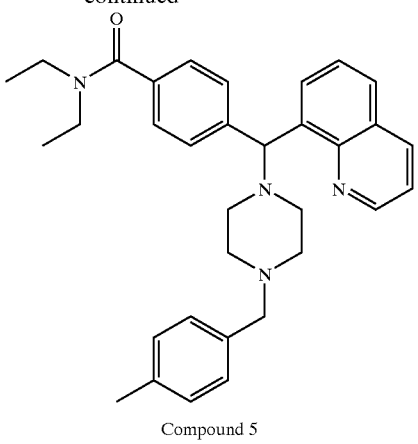

Compound 5

To a solution of compound 1 (0.80 g; 1.99 mmol) in $CH_2Cl_2$ (20 ml) was added $Et_3N$ (0.83 ml; 5.97 mmol) followed by p-methyl benzyl bromide (773 mg; 4.18 mmol). The reaction mixture was stirred overnight and was then was concentrated under reduced pressure. Purification by reverse phase using 10%–30% $CH_3CN/H_2O$.

(M+1) calculated: 507.70, (M+1) observed: 507.20

IR (NaCl, free amine) 2969, 2807, 2360, 1628, 1455, 1425, 1286, 1134, 1095 (cm-1).

$^1$H NMR ($CDCl_3$, free amine) δ=1.0, 1.1 (2m, 6H, amide-Me), 2.31 (s, 3H, Ar-Me), 2.5 (m, 8H, piperazine-H), 3.2, 3.5 (2m, amide-$CH_2$), 3.49 (s, 2H, Ar$CH_2$N), 6.03 (s, 1H, Ar2CH), 7.06–7.68 (m, 11H, Ar—H), 8.01–8.12 (m, 2H, Ar—H), 8.93 (m, 1H, Ar—H).

Anal. ($C_{32}H_{38}Cl_2N_4O$) C, H, N.

Examples 5 & 6

Separation of the Enantiomers of Compound 5 to Give Compounds 6 and 7

The preparative separation of this compound was done on a semi preparative Chiralcel AD column (21 mm×25 cm) using Hexane/EtOH/Diethylamine 80:20:0.1 as the mobile phase. On the Chiralcel AD column, the (−)-isomer was found to elute first.

Example 5

(−)4-[[4-(4-methylbenzyl)-1-piperazinyl](8-quinolinyl)methyl]-N,N-diethylbenzamide (Compound 6)

$[\alpha]_D^{25}$:: −131° (c 1.0, MeOH)

Example 6

(+)4-[[4-(4-methylbenzyl)-1-piperazinyl](8-quinolinyl)methyl]-N,N-diethylbenzamide (compound 7)

$[\alpha]_D^{25}$: +124° (c 1.4, MeOH)

Example 7

Preparation of 4-[{4-[4-(tert-butyl)benzyl]-1-piperazinyl}(8-quinolinyl)methyl]-N,N-diethylbenzamide Dihydrochloride (Compound 8)

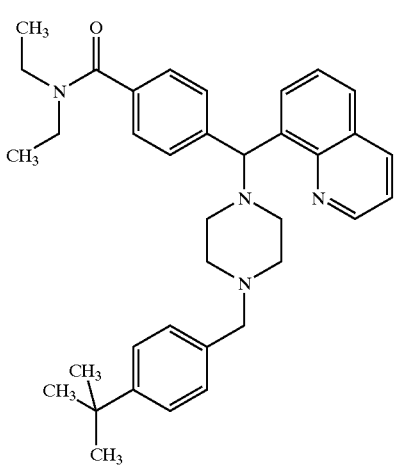

Compound 8

By procedure analogous to the preparation of compound 2, the title compound 8 was prepared. Alkylation was performed with 4-tert-butylbenzylbromide.
MS (ES) 549.53 (MH+).
IR (NaCl, free amine) 2963, 2807, 2360, 1631, 1456, 1425, 1285, 1135, 1094, 1001 (cm$^{-1}$)
$^1$H NMR (CDCl$_3$, free amine) δ=1.0, 1.2 (2m, 6H), 1.29 (s, 9H), 2.50 (m, 8H), 3.2, 3.5 (2m), 3.50 (s, 2H), 6.04 (s, 1H), 7.16–7.68 (m, 11H), 7.98–8.10 (m, 2H), 8.92 (m, 1H). Anal. (C$_{36}$H$_{46}$Cl$_2$N$_4$O) C, H, N.

Example 8
Preparation of N,N-diethyl-4-[[4-(4-nitrobenzyl)-1-piperazinyl](8-quinolinyl)methyl]benzamide Dihydrochloride (Compound 9)

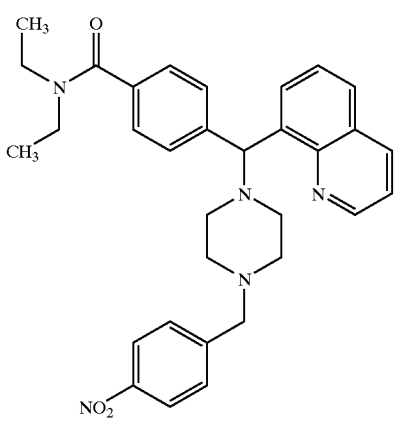

Compound 9

By procedure analogous to the preparation of compound 2 above, the title compound 9 was prepared. Alkylation was performed with 4-nitrobenzylbromide.
MS (ES) 538.04 (MH+).
IR (NaCl, free amine) 2969, 2809, 2360, 1626, 1518, 1456, 1426, 1343, 1286, 1134, 1095, 1001 (cm-1).
$^1$H NMR (CDCl3, free amine) δ=1.0, 1.2 (2m, 6H), 2.50 (m, 8H), 3.2, 3.5 (2m), 3.60 (s, 2H), 6.05 (s, 1H), 7.18–8.16 (m, 13H), 8.94 (m, 1H).
Anal. (C$_{32}$H$_{37}$Cl$_2$N$_5$O$_3$) C, H, N.

Example 9
Preparation of 4-[{4-[2,4-bis(trifluoromethyl)benzyl]-1-piperazinyl}(8-quinolinyl)methyl]-N,N-diethylbenzamide Dihydrochloride (Compound 10)

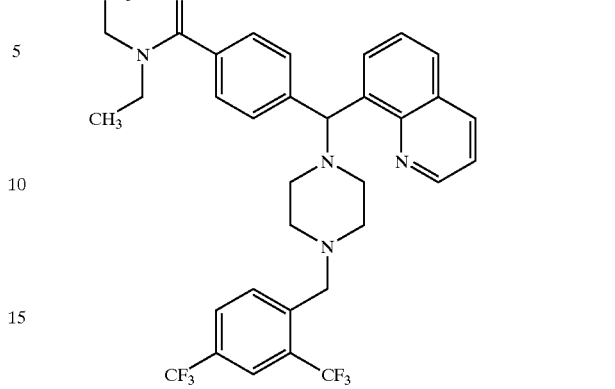

Compound 10

By following the procedure analogous to the preparation of compound 2 above, the title compound 10 was prepared. Alkylation was performed with 2,4-bis(trifluoromethyl)benzylbromide.
MS (ES) 629.08 (MH+).
IR (NaCl, free amine) 2970, 2811, 2360, 1628, 1456, 1426, 1346, 1275, 1170, 1128 (cm$^{-1}$).
$^1$H NMR (CDCl3, free amine) δ=1.0, 1.2 (2m, 6H), 2.48 (m, 8H), 3.2, 3.5 (2m), 3.71 (s, 2H), 6.06 (s, 1H), 7.20–8.14 (m, 12H), 8.95 (m, 1H). Anal. (C$_{34}$H$_{36}$Cl$_2$F$_6$N$_4$O) C, H, N Example 10
Preparation of N,N-diethyl-4-[[4-(4-methoxybenzyl)-1-piperazinyl](8-quinolinyl)methyl]benzamide Dihydrochloride (Compound 11)

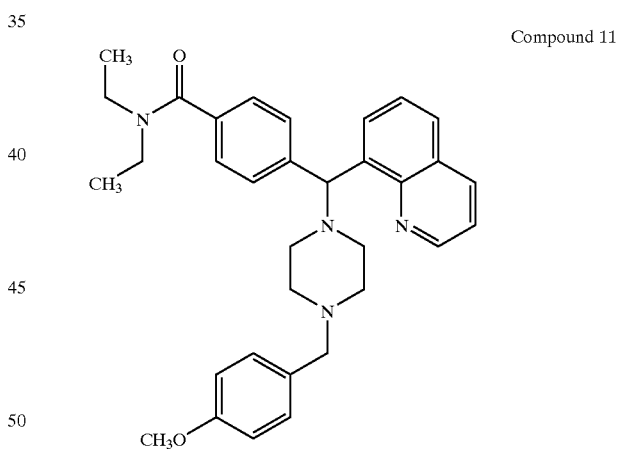

Compound 11

By procedure analogous to the preparation of compound 2 above, the title compound 11 was prepared. Alkylation was performed with 4-methoxybenzylchloride.
MS (ES) 523.45 (MH+).
IR (NaCl, free amine) 2966, 2806, 2360, 1627, 1510, 1456, 1426, 1286, 1246, 1134, 1095 (cm-1).
$^1$H NMR (CDCl3, free amine) δ=1.0, 1.2 (2m, 6H), 2.48 (m, 8H), 3.2, 3.5 (2m), 3.47 (s, 2H), 3.78 (s, 3H), 6.03 (s, 1H), 6.80–7.68 (m, 11H), 8.01–8.12 (m, 2H), 8.93 (m, 1H). Anal. (C$_{33}$H$_{40}$Cl$_2$N$_4$O$_2$) C, H, N.

Example 11
Preparation 4-[[4-(2,4-dichlorobenzyl)-1-piperazinyl](8-quinolinyl)methyl]-N,N-diethylbenzamide Dihydrochloride (Compound 12)

Compound 12

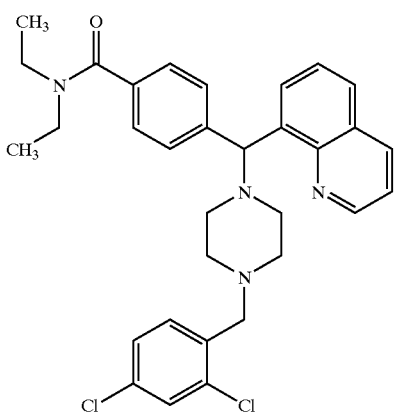

By following the procedure analogous to the preparation of compound 2 above, the title compound 12 was prepared. Alkylation was performed with 2,4-dichlorobenzylchloride.

MS (ES) 562.45 (MH+).
IR (NaCl, free amine) 2968, 2810, 2360, 2341, 1627, 1470, 1426, 1285, 1134, 1095 (cm$^{-1}$)
$^1$H NMR (CDCl3, free amine) δ=1.0, 1.1 (2m, 6H), 2.5 (m, 8H), 3.2, 3.5 (2m), 3.58 (s, 2H), 6.05 (s, 1H), 7.14–7.70 (m, 10H), 8.06 (m, 2H), 8.94 (m, 1H). Anal. ($C_{32}H_{36}Cl_4N_4O$) C, H, N.

Example 12
Preparation of N,N-diethyl-4-[[4-(2-pyridinylmethyl)-1-piperazinyl](8-quinolinyl)methyl]benzamide Dihydrochloride (Compound 13)

Compound 13

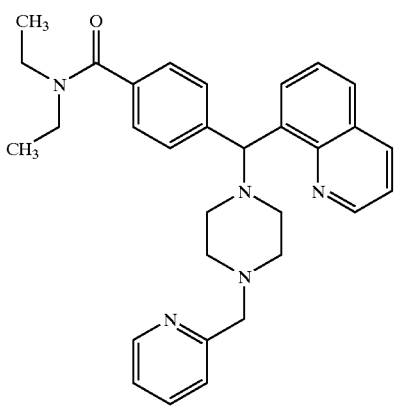

Compound 1 (80 mg, 0.20 mmol) was dissolved in MeOH (2 mL) with 2-pyridylcarboxaldehyde (39 μL, 0.40 mmol) and HOAc (1 μL, 0.02 mmol). Sodium cyanoborohydride (26 mg, 0.40 mmol) was added and stirring continued for 48 h. Solvent was evaporated and residue purified by chromatography on silica (0–10% MeOH in CH$_2$Cl$_2$). 38 mg (39%) product was obtained.

MS (ES) 494.19 (MH+).
IR (NaCl, free amine) 2968, 2809, 2360, 1626, 1455, 1428, 1286, 1134, 1094, 1001 (cm-1).
$^1$H NMR (CDCl3, free amine) δ=1.0, 1.2 (2m, 6H), 2.50 (m, 8H), 3.2, 3.5 (2m), 3.69 (s, 2H), 6.05 (s, 1H), 7.12–7.70 (m, 10H), 8.08 (m, 2H), 8.54 (m, 1H), 8.94 (m, 1H). Anal. ($C_{31}H_{37}Cl_2N_5O$) C, H, N.

Example 13
Preparation of N,N-diethyl-4-[[4-(3-thienylmethyl)-1-piperazinyl](8-quinolinyl)methyl]benzamide (Compound 14)

The title compound 14 was prepared by following the synthetic procedure of Scheme 3 below.

Scheme 3

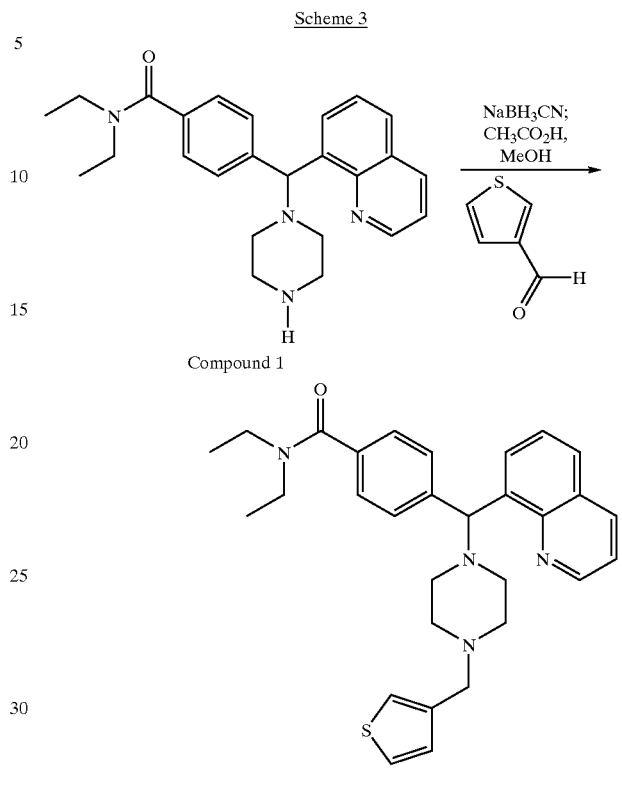

Compound 1

Compound 14

To a solution of compound 1 (500 mg; 0.99 mmol) in methanol (10 ml) was added thiophene 3-carboxaldehyde (104 ul; 1.19 mmol) followed by acetic acid (0.1 ml; 1%) and sodium cyano borohydride (186.6 mg; 2.97 mmol). The reaction mixture was stirred overnight, then sodium hydroxide 2N was added and the mixture extracted with methylene chloride (3x). The combined methylene chloride extracts were dried over Na$_2$SO$_4$, filtered and concentrated under reduced pressure. Purification by reverse phase using 10%–30% CH$_3$CN/H$_2$O (TFA as the buffer) gave 258 mg of desired product (TFA salt).

HPLC purity: >99% (215 nm); >95% (254 nm)
(M+1) calculated: 499.25, (M+1) observed: 499.46
Anal.: calculated for ($C_{30}H_{34}N_4OS$ X 2.80 $C_2HO_2F_3$ X 1.80H$_2$O): C: 50.28%; H: 4.79%; N: 6.59%; O: 15.80%; S: 3.77%; F: 18.77% found: C: 50.28%; H: 4.83%; N: 6.53%
$^1$HNMR: 8.95 (dd, 1H, J=4.4, 2.0 Hz), 8.38 (dd, 1H, J=8.0, 2.0 Hz), 8.00 (dd, 1H, J=7.2, 1.6 Hz), 7.84 (dd, 1H, J=8.0, 1.6 Hz), 7.52–7.62 (m, 5H), 7.45 (dd, 1H, J=4.8, 2.8 Hz), 7.20 (dd, 2H, J=8.8, 2.2 Hz), 7.11 (dd, 1H, J=4.8, 1.6 Hz), 5.96 (s, 1H), 4.27 (s, 2H), 3.34–3.44 (m, 2H), 3.22–3.28 (m, 4H), 3.04–3.14 (m, 2H), 2.66–2.88 (m, 4H), 1.04–1.14 (m, 3H), 0.88–0.98 (m, 3H)

Example 14
Preparation of N,N-diethyl-4-[[4-(2-furanylmethyl)-1-piperazinyl](8-quinolinyl)methyl]benzamide (Compound 15)

The title compound 15 was prepared by following the synthetic procedure of Scheme 4 below.

Scheme 4

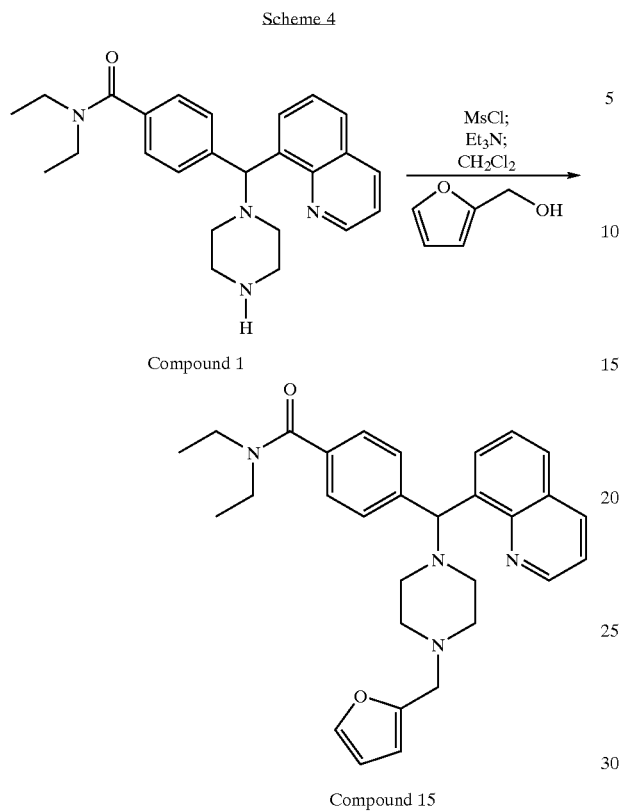

Compound 1

Compound 15

Scheme 5

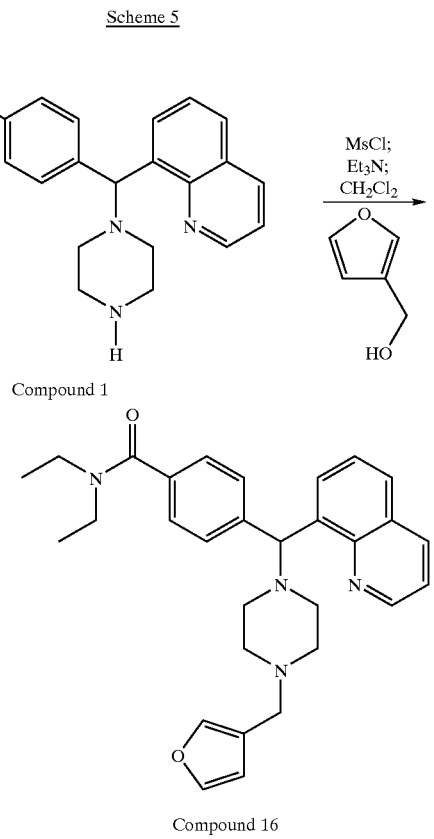

Compound 1

Compound 16

To a 0° C. solution of furfurylalcohol (0.19 ml; 2.24 mmol) and triethylamine (0.52 ml; 3.73 mmol) in methylene chloride (4 ml) was added methanesulfonyl chloride (0.17 ml; 2.24 mmol). The mixture was stirred 1 hour at 0° C., then compound 1 (300 mg; 0.75 mmol) was added. The reaction mixture was allowed to warm to room temperature and stirred overnight, then heated to 45° C. and stirred for 1½ hours. The reaction mixture was allowed to cool to room temperature and NaOH 2N was added untill pH was basic. The mixture was extracted with methylene chloride (3×). The combined methylene chloride extracts were dried over $Na_2SO_4$, filtered and concentrated under reduced pressure. Purification by reverse phase using 10%–25% $CH_3CN/H_2O$ (TFA as the buffer) gave 197 mg of desired product (TFA salt).

HPLC purity: >99% (215 nm, 254 nm and 280 nm)

(M+1) calculated: 483.63, (M+1) observed: 483.30

$^1$HNMR: 8.89 (dd, 1H, J=4.4, 1.6 Hz), 8.29 (dd, 1H, J=8.0, 1.6 Hz), 7.97 (dd, 1H, J=7.2, 1.6 Hz), 7.79 (d, 1H, J=7.2 Hz), 7.61 (d, 2H, J=8.0 Hz), 7.52–7.58 (m, 2H), 7.48 (dd, 1H, J=8.0, 4.4 Hz), 7.19 (d, 2H, J=8.0 Hz), 6.56 (d, 1H, J=3.2 Hz), 6.40 (dd, 1H, J=3.2, 2.4 Hz), 6.02 (s, 1H), 4.26 (s, 2H), 3.34–3.44 (m, 2H), 3.16–3.26 (m, 4H), 3.04–3.14 (m, 2H), 2.68–2.86 (m, 4H), 1.06–1.14 (m, 3H), 0.90–0.98 (m, 3H)

Example 15

5 Preparation of N,N-diethyl-4-[[4-(3-furanylmethyl)-1-piperazinyl](8-quinolinyl)methyl]benzamide (Compound 16)

The title compound 16 was prepared by following the synthetic procedure of Scheme 5 below.

To a 0° C. solution of 3-furanmethanol (220 mg; 2.24 mmol) and triethylamine (0.52 ml; 3.73 mmol) in methylene chloride (4 ml) was added methanesulfonyl chloride (0.17 ml; 2.24 mmol). The mixture was stirred 1 hour at 0° C., then compound 1 (300 mg; 0.75 mmol) was added. The reaction mixture was allowed to warm to room temperature and stirred overnight, then heated to 45° C. and stirred for 3½ hours. The reaction mixture was allowed to cool to room temperature and NaOH 2N was added untill pH was basic. The mixture was extracted with methylene chloride (3×). The combined methylene chloride extracts were dried over $Na_2SO_4$, filtered and concentrated under reduced pressure. Purification by reverse phase using 10%–25% $CH_3CN/H_2O$ (TFA as the buffer) gave 293 mg of desired product (TFA salt).

HPLC purity: >98% (215 nm and 280 nm); >99% (254 nm)

(M+1) calculated: 483.63, (M+1) observed: 483.34

Anal.: calculated for ($C_{30}H_{34}N_4O_2$ X 3.10 $C_2HO_2F_3$ X 1.70$H_2O$): C: 50.17%; H: 4.71%; N: 6.46%; 0:18.27%; F: 20.39% found: C: 50.14%; H: 4.76%; N: 6.38%

$^1$HNMR: 8.93 (dd, 1H, J=4.4, 2.0 Hz), 8.36 (dd, 1H, J=8.6, 2.0 Hz), 8.00 (dd, 1H, J=7.4, 1.2 Hz), 7.82 (dd, 1H, J=7.6, 1.2 Hz), 7.48–7.66 (m, 6H), 7.19 (d, 2H, J=8.0 Hz), 6.46 (s, 1H), 5.97 (s, 1H), 4.13 (s, 2H), 3.32–3.44 (m, 2H), 3.20–3.28 (m, 4H), 3.04–3.14 (m, 2H), 2.66–2.86 (m, 4H), 1.04–1.14 (m, 3H), 0.88–0.98 (m, 3H)

Example 16

Preparation of N,N-diethyl-4-[[4-(2-thiophenylmethyl)-1-piperazinyl](8-quinolinyl)methyl]benzamide Dihydrochloride (Compound 17)

The title compound 17 was prepared by following the synthetic procedure of Scheme 6 below.

Scheme 6

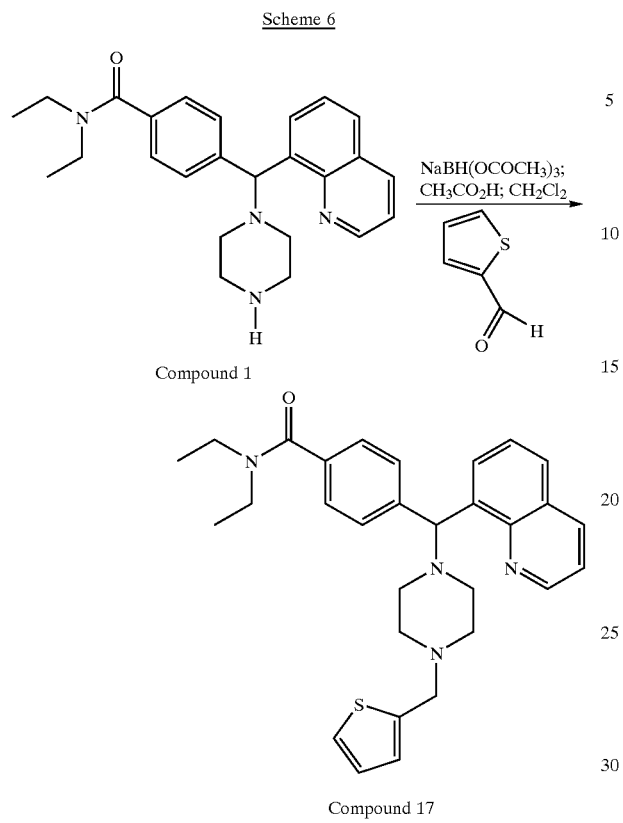

Compound 1

Compound 17

Scheme 7

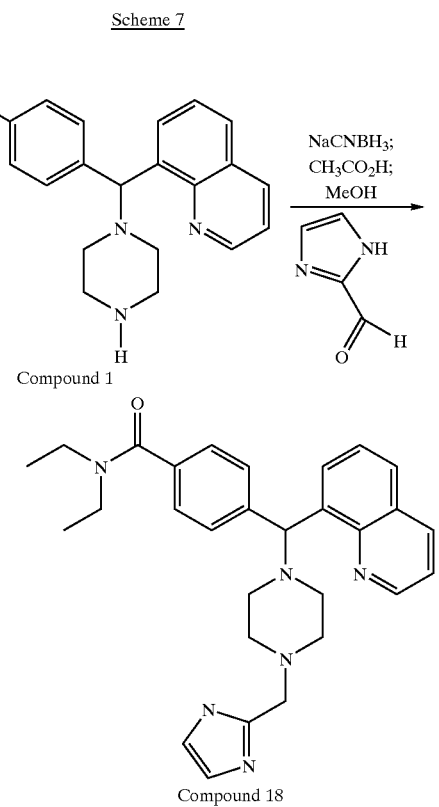

Compound 1

Compound 18

To a solution of compound 1 (0.99 mmol) in methylene chloride (10 ml) was added 2-thiophenecarboxaldehyde (190 ul; 1.98 mmol) followed by acetic acid (0.1 ml; 1%). The mixture was stirred 30 minutes then sodium triacetoxyborohydride (0.63 g; 2.97 mmol) was added and the reaction mixture stirred overnight. The reaction mixture was neutralized with sodium hydroxide 2N and extracted with methylene chloride (3×). The combined methylene chloride extracts were dried over $Na_2SO_4$, filtered and concentrated under reduced pressure. Purification by reverse phase using 10%–30% $CH_3CN/H_2O$ (TFA as the buffer) gave 115 mg of desired product (TFA salt).

HPLC purity: >99% (215 nm); >96% (254 nm)

(M+1) calculated: 499.25, (M+1) observed: 499.33

Anal.: calculated for ($C_{30}H_{34}N_4OS$ X 2.50 $C_2HO_2F_3$ X 0.10$H_2O$): C: 53.51%; H: 4.71%; N: 7.13%; 0:12.42%; S: 4.08%; F: 18.14% found: C: 53.49%; H: 4.63%; N: 7.49%

$^1$HNMR: 8.91 (dd, 1H, J=4.0, 1.6 Hz), 8.30 (dd, 1H, J=8.8, 1.6 Hz), 7.96 (dd, 1H, J=7.4, 1.4 Hz), 7.81 (d, 1H, J=7.2 Hz), 7.62 (d, 2H, J=8.0 Hz), 7.46–7.58 (m, 3H), 7.20 (d, 2H, J=8.0 Hz), 7.14–7.22 (m, 1H), 7.00 (dd, 1H, J=5.2, 3.6 Hz), 6.03 (s, 1H), 4.38 (s, 2H), 3.34–3.44 (m, 2H), 3.14–3.22 (m, 4H), 3.06–3.12 (m, 2H), 2.74–2.88 (m, 4H), 1.04–1.14 (m, 3H), 0.88–0.98 (m, 3H)

Example 17

Preparation of N,N-diethyl-4-[[4-(2-imidazolylmethyl)-1-piperazinyl](8-quinolinyl)methyl]benzamide Dihydrochloride (Compound 18)

The title compound 18 was prepared by following the synthetic procedure of Scheme 7 below.

To a solution of compound 1 (0.99 mmol) in methanol (10 ml) was added 2-imidazolecarboxaldehyde (114 mg; 1.19 mmol) followed by acetic acid (0.5 ml; 5%). The mixture was stirred 3 hours then sodium cyanoborohydride (186.6 mg; 2.97 mmol) was added and the reaction mixture was stirred overnight. The reaction mixture was neutralized with sodium hydroxide 2N and extracted with methylene chloride (3×). The combined methylene chloride extracts were dried over $Na_2SO_4$, filtered and concentrated under reduced pressure. Purification by reverse phase using 10%–30% $CH_3CN/H_2O$ (TFA as the buffer) gave the TFA salt. The HCl salt was made using HCl/ether. Yield: 60.3 mg of desired product (HCl salt).

HPLC purity: >95% (215 nm); >93% (254 nm)

(M+1) calculated: 483.29, (M+1) observed: 483.19

$^1$HNMR: 9.12–9.22 (m, 1H), 8.54–8.62 (m, 1H), 8.08–8.16 (m, 1H), 7.98–8.04 (m, 1H), 7.60–7.86 (m, 4H), 7.38–7.46 (m, 2H), 7.22–7.32 (m, 2H), 6.32 (s, 1H), 4.11 (s, 2H), 2.94–3.40 (m, 12H), 0.88–1.12 (m, 6H).

Example 18

Preparation of N,N-diethyl-4-[[4-(4-imidazolylmethyl)-1-piperazinyl](8-quinolinyl)methyl]benzamide Dihydrochloride (Compound 19)

The title compound 19 was prepared by following the synthetic procedure of Scheme 8 below.

Scheme 8

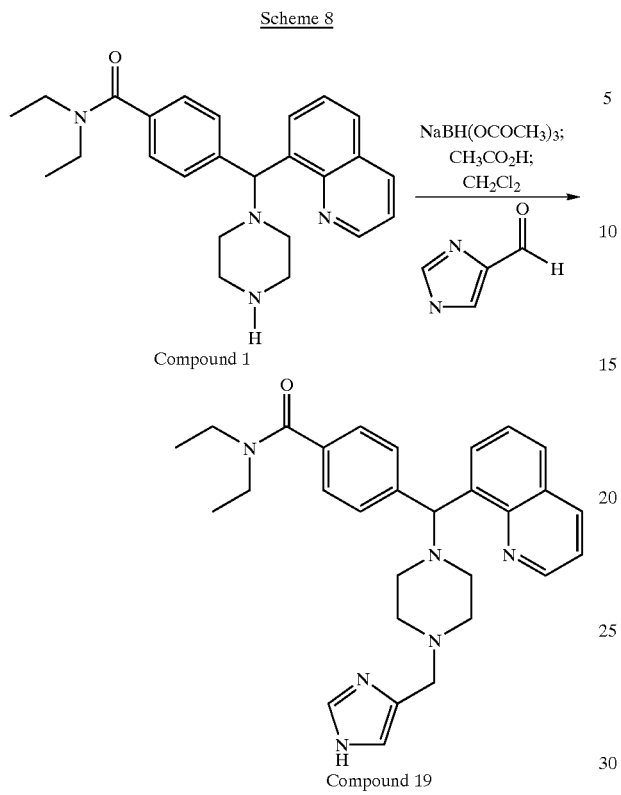

Scheme 9

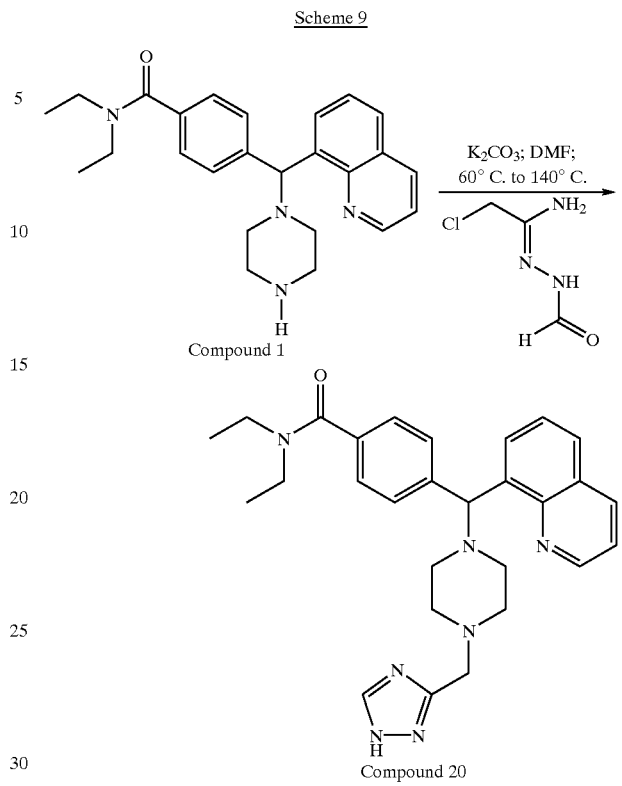

To a room temperature solution of 434 (400 mg; 0.99 mmol) and 4-imidazole carboxaldehyde (95.5 mg; 0.99 mmol) in methylene chloride (10 ml) was added acetic acid (0.1 ml). The mixture was stirred for 5 hours then sodium triacetoxyborohydride (632 mg; 2.98 mmol) was added. The reaction mixture was stirred overnight and was neutralized with sodium hydroxide 2N. The mixture was extracted with methylene chloride (3×). The combined methylene chloride extracts were dried over $Na_2SO_4$, filtered and concentrated under reduced pressure. Purification by reverse phase chromatography using 15% $CH_3CN/H_2O$ (TFA as the buffer) gave 103 mg of desired product (TFA salt).

HPLC purity: >99% (215 nm, 254 nm and 280 nm)

(M+1) calculated: 483.28, (M+1) observed: 482.96

Anal.: calculated for ($C_{29}H_{34}N_6O$ X 3.80 $C_2HO_2F_3$ X 0.80$H_2O$): C: 47.25%; H: 4.27%; N: 9.03%; O:16.17%; F: 23.28% found: C: 47.31%; H: 4.40%; N: 8.87

$^1$HNMR: 8.99 (dd, 1H, J=4.4, 1.2 Hz), 8.76 (d, 1H, J=1.2 Hz), 8.39 (dd, 1H, H=8.8, 1.2 Hz), 7.93 (dd, 1H, J=7.2, 1.6 Hz), 7.86 (dd, 1H, J=8.0, 1.6 Hz), 7.71 (d, 2H, J=8.8 Hz), 7.60 (dd, 1H, J=8.8, 4.4 Hz), 7.56 (dd, 1H, J=8.0, 7.2 Hz), 7.40 (s, 1H), 7.27 (d, 2H, J=8.8 Hz), 6.12 (s, 1H) 3.74 (s, 2H), 3.38 (q, 2H, J=6.4 Hz), 3.10–3.25 (m, 6H), 3.06 (q, 2H, J=7.2 Hz), 2.75–2.90 (m, 2H), 1.08 (t, 3H, J=6.4 Hz), 0.92 (t, 3H, J=7.2 Hz)

Example 19

Preparation of N,N-diethyl-4-[[4-(3-triazolylmethyl)-1-piperazinyl](8-quinolinyl)methyl]benzamide Dihydrochloride (Compound 20)

The title compound 20 was prepared by following the synthetic procedure of Scheme 9 below.

To a room temperature solution 434 (200 mg; 0.50 mmol) in dimethylformamide (10 ml) was added potassium carbonate (275 mg; 1.99 mmol), followed by N-formamido-2-(chloromethyl)acetamidine (170 mg; 1.24 mmol). The reaction mixture was heated to 60° C. and stirred for 2 days, then the temperature was raised to 140° C. and stirred for 3 hours. The reaction mixture was allowed to cool to room temperature and water was added. The mixture was extracted with ethylacetate (3×). The combined ethylacetate extracts were dried over $Na_2SO_4$, filtered and concentrated under reduced pressure. Purification by reverse phase chromatography using 20% $CH_3CN/H_2O$ (TFA as the buffer) gave 21 mg of desired product (TFA salt).

HPLC purity: >99% (215 nm, 254 nm and 280 nm)

(M+1) calculated: 484.28, (M+1) observed: 483.92

Anal.: calculated for ($C_{28}H_{33}N_7O$ X 3.30 $C_2HO_2F_3$ X 3.30$H_2O$): C: 45.20%; H: 4.70%; N: 10.66%; 0:18.97%; F: 20.46% found: C: 45.12%; H: 4.60%; N: 10.84

$^1$HNMR: 8.94 (dd, 1H, J=4.4, 1.6 Hz), 8.38 (s, 1H), 8.33 (dd, 1H, J=8.0, 1.2 Hz), 7.93 (d, 1H, J=7.2 Hz), 7.85 (d, 1H, J=7.2 Hz), 7.65 (d, 2H, J=8.8 Hz), 7.51–7.58 (m, 2H), 7.23 (d, 2H, J=8.8 Hz), 6.15 (s, 1H), 4.21 (s, 2H), 3.40–3.50 (m, 2H), 3.10–3.30 (m, 8H), 2.90–3.10 (m, 2H), 0.90–1.30 (m, 6H)

Pharmaceutical Compositions

The novel compounds according to the present invention may be administered orally, intramuscularly, subcutaneously, topically, intranasally, intraperitoneally, intrathoracially, intravenously, epidurally, intrathecally, intracerebroventricularly and by injection into the joints.

A preferred route of administration is orally, intravenously or intramuscularly.

The dosage will depend on the route of administration, the severity of the disease, age and weight of the patient and other factors normally considered by the attending physician, when determining the individual regimen and dosage level as the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Pharmaceutically acceptable salts are acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, benzathine, chloroprocaine, choline, diethanolamine, ethylenediamine, meglumine, procaine, aluminium, calcium, lithium, magnesium, potassium, sodium, and zinc. Preferred pharmaceutically acceptable salts are the hydrochlorides, and bitartrates. The hydrochloride salts are particularly preferred.

The term composition is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid from compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical compositions is in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Biological Evaluation

In vitro Model

Cell Culture

Human 293S cells expressing cloned human $\mu$, $\delta$, and $\kappa$ receptors and neomycin resistance were grown in suspension at 37° C. and 5% $CO_2$ in shaker flasks containing calcium-free DMEM10% FBS, 5% BCS, 0.1% Pluronic F-68, and 600 $\mu$g/ml geneticin.

Membrane Preparation

Cells were pelleted and resuspended in lysis buffer (50 mM Tris, pH 7.0, 2.5 mM EDTA, with PMSF added just prior to use to 0.1 mM from a 0.1 M stock in ethanol), incubated on ice for 15 min, then homogenized with a polytron for 30 sec. The suspension was spun at 1000 g (max) for 10 min at 4° C. The supernatant was saved on ice and the pellets resuspended and spun as before. The supernatants from both spins were combined and spun at 46,000 g (max) for 30 min. The pellets were resuspended in cold Tris buffer (50 mM Tris/Cl, pH 7.0) and spun again. The final pellets were resuspended in membrane buffer (50 mM Tris, 0.32 M sucrose, pH 7.0). Aliquots (1 ml) in polypropylene tubes were frozen in dry ice/ethanol and stored at −70° C. until use. The protein concentrations were determined by a modified Lowry assay with SDS.

Binding Assays

Membranes were thawed at 37° C., cooled on ice, passed 3 times through a 25-gauge needle, and diluted into binding buffer (50 mM Tris, 3 mM $MgCl_2$, 1 mg/ml BSA (Sigma A-7888), pH 7.4, which was stored at 4° C. after filtration through a 0.22 m filter, and to which had been freshly added 5 $\mu$g/ml aprotinin, 10 $\mu$M bestatin, 10 $\mu$M diprotin A, no DTT). Aliquots of 100 $\mu$l (for $\mu$g protein, see Table 1) were added to iced 12×75 mm polypropylene tubes containing 100 $\mu$l of the appropriate radioligand (see Table 1) and 100 $\mu$l of test peptides at various concentrations. Total (TB) and nonspecific (NS) binding were determined in the absence and presence of 10 $\mu$M naloxone respectively. The tubes were vortexed and incubated at 25° C. for 60–75 min, after which time the contents are rapidly vacuum-filtered and washed with about 12 ml/tube iced wash buffer (50 mM Tris, pH 7.0, 3 mM $MgCl_2$) through GF/B filters (Whatman) presoaked for at least 2 h in 0.1% polyethyleneimine. The radioactivity (dpm) retained on the filters was measured with a beta counter after soaking the filters for at least 12 h in mini vials containing 6–7 ml scintillation fluid. If the assay is set up in 96-place deep well plates, the filtration is over 96-place PEI-soaked unifilters, which were washed with 3×1 ml wash buffer, and dried in an oven at 55° C. for 2 h. The filter plates were counted in a TopCount (Packard) after adding 50 $\mu$l MS-20 scintillation fluid/well.

Data Analysis

The specific binding (SB) was calculated as TB-NS, and the SB in the presence of various test peptides was expressed as percentage of control SB. Values of $IC_{50}$ and Hill coefficient ($n_H$) for ligands in displacing specifically bound radioligand were calculated from logit plots or curve fitting programs such as Ligand, GraphPad Prism, SigmaPlot, or ReceptorFit. Values of $K_i$ were calculated from the Cheng-Prussoff equation. Mean±S.E.M. values of $IC_{50}$, $K_i$ and $n_H$ were reported for ligands tested in at least three displacement curves. Biological data are reported below in Table 1.

TABLE 1

Summary of biological data

| Example # | HDELTA | HDELTA EC50 | HDELTA % EMAX | RAT BRAIN EC50 | RAT BRAIN % EMAX | MOUSE BRAIN EC50 | MOUSE BRAIN % EMAX | MLM 10000 % rem. | MLM 100000 % rem. | RLM 10000 % rem. | RLM 100000 % rem. |
|---|---|---|---|---|---|---|---|---|---|---|---|
| 12 | 0.692 | 0.76 | 97.73 | 20.99 | 106.43 | 27.14 | 91.34 | 0 | 53.5 | 21.5 | 66 |
| 13 | 1.033 | 1.44 | 101.18 | 17.7 | 111.96 | 25.77 | 112.68 | 1.667 | 71.667 | 10 | 62.667 |
| 14 | 0.181 | 0.76 | 88.65 | 14.26 | 102.02 | 20.49 | 106.48 | 0 | 49 | 13.5 | 84.5 |
| 15 | 0.787 | 0.79 | 88.99 | 14.16 | 108.81 | 16.01 | 109.85 | 0 | 68 | 10 | 86 |
| 16 | 1.509 | 2.39 | 99.36 | 30.83 | 100.5 | 24.2 | 98.41 | 0.5 | 46.5 | 9.5 | 64.5 |
| 17 | 1.091 | 3.03 | 95.66 | 49.47 | 105.91 | 75.1 | 92.47 | 0 | 21.5 | 5.5 | 75 |
| 18 | 1.54 | 5.85 | 93.82 | 452.31 | 111.01 | 429.56 | 108.41 | | | | |
| 19 | 18.751 | 85.24 | 97.88 | 2807.47 | 56.35 | 1365.82 | 48.68 | | | | |

Receptor Saturation Experiments

Radioligand Kδ values were determined by performing the binding assays on cell membranes with the appropriate radioligands at concentrations ranging from 0.2 to 5 times the estimated Kδ (up to 10 times if amounts of radioligand required are feasable). The specific radioligand binding was expressed as pmole/mg membrane protein. Values of Kδ and $B_{max}$ from individual experiments were obtained from non-linear fits of specifically bound (B) vs. nM free (F) radioligand from individual according to a one-site model.

Determination of Mechano-Allodynia Using Von Frey Testing

Testing was performed between 08:00 and 16 00 h using the method described by Chaplan et al. (1994). Rats were placed in Plexiglas cages on top of a wire mesh bottom which allowed access to the paw, and were left to habituate for 10–15 min. The area tested was the mid-plantar left hind paw, avoiding the less sensitive foot pads. The paw was touched with a series of 8 Von Frey hairs with logarithmically incremental stiffness (0.41, 0.69, 1.20, 2.04, 3.63, 5.50, 8.51, and 15.14 grams; Stoelting, Ill., USA). The von Frey hair was applied from underneath the mesh floor perpendicular to the plantar surface with sufficient force to cause a slight buckling against the paw, and held for approximately 6–8 seconds. A positive response was noted if the paw was sharply withdrawn. Flinching immediately upon removal of the hair was also considered a positive response. Ambulation was considered an ambiguous response, and in such cases the stimulus was repeated.

Testing Protocol

The animals were tested on postoperative day 1 for the FCA-treated group. The 50% withdrawal threshold was determined using the up-down method of Dixon (1980). Testing was started with the 2.04 g hair, in the middle of the series. Stimuli were always presented in a consecutive way, whether ascending or descending. In the absence of a paw withdrawal response to the initially selected hair, a stronger stimulus was presented; in the event of paw withdrawal, the next weaker stimulus was chosen. Optimal threshold calculation by this method requires 6 responses in the immediate vicinity of the 50% threshold, and counting of these 6 responses began when the first change in response occurred, e.g. the threshold was first crossed. In cases where thresholds fell outside the range of stimuli, values of 15.14 (normal sensitivity) or 0.41 (maximally allodynic) were respectively assigned. The resulting pattern of positive and negative responses was tabulated using the convention, X=no withdrawal; O=withdrawal, and the 50% withdrawal threshold was interpolated using the formula:

$$50\% \text{ g threshold} = 10^{(Xf+k\delta)}/10,000$$

where Xf=value of the last von Frey hair used (log units); k=tabular value (from Chaplan et al. (1994)) for the pattern of positive/negative responses; and δ=mean difference between stimuli (log units). Here δ=0.224.

Von Frey thresholds were converted to percent of maximum possible effect (% MPE), according to Chaplan et al. 1994. The following equation was used to compute % MPE:

$$\% \text{ MPE} = \frac{\text{Drug treated threshold (g)} - \text{allodynia threshold (g)}}{\text{Control threshold (g)} - \text{allodynia threshold (g)}} \times 100$$

Administration of Test Substance

Rats were injected (subcutaneously, intraperitoneally, intravenously or orally) with a test substance prior to von Frey testing, the time between administration of test compound and the von Frey test varied depending upon the nature of the test compound.

Writhing Test

Acetic acid will bring abdominal contractions when administered intraperitoneally in mice. These will then extend their body in a typical pattern. When analgesic drugs are administered, this described movement is less frequently observed and the drug selected as a potential good candidate.

A complete and typical Writhing reflexe is considered only when the following elements are present: the animal is not in movement; the lower back is slightly depressed; the plantar aspect of both paws is observable.

(i) Solutions Preparation

Acetic acid (AcOH): 120 μL of Acetic Acid is added to 19.88 ml of distilled water in order to obtain a final volume of 20 ml with a final concentration of 0.6% AcOH. The solution is then mixed (vortex) and ready for injection.

Compound (drug): Each compound is prepared and dissolved in the most suitable vehicle according to standard procedures.

(ii) Solutions Administration

The compound (drug) is administered orally, intraperitoneally (i.p.), subcutaneously (s.c.) or intravenously (i.v.)) at. 10 ml/kg (considering the average mice body weight) 20, 30 or 40 minutes (according to the class of compound and its characteristics) prior to testing. When the compound is delivered centrally: Intraventricularly (i.c.v.) or intrathecally (i.t.) a volume of 5 μL is administered.

The AcOH is administered intraperitoneally (i.p.) in two sites at 10 ml/kg (considering the average mice body weight) immediately prior to testing.

(iii) Testing

The animal (mouse) is observed for a period of 20 minutes and the number of occasions (Writhing reflex) noted and compiled at the end of the experiment. Mice are kept in individual "shoe box" cages with contact bedding. A total of 4 mice are usually observed at the same time: one control and three doses of drug.

What is claimed is:

1. A compound according to formula I

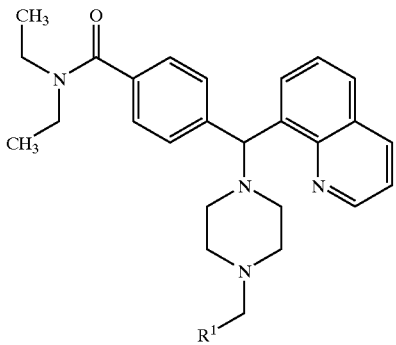

wherein
R¹ is selected from
(i) phenyl;
(ii) pyridinyl

(iii) thiophenyl

(iv) furanyl

(v) imidazolyl

(vi) triazolyl

where each phenyl ring and heteroaromatic ring may optionally and independently be further substituted by 1, 2 or 3 substituents selected from straight and branched $C_1$–$C_6$ alkyl, $NO_2$, $CF_3$, $C_1$–$C_6$ alkoxy, chloro, fluoro, bromo, and iodo;

as well as pharmaceutically acceptable salts thereof and enantiomers thereof.

2. A compound according to claim 1, wherein the optional substituent(s) on the aromatic or the heteroaromatic ring(s) is selected from anyone of $NO_2$, iso-butyl, $CF_3$, methoxy, methyl, or chloro.

3. A compound according to claim 1 or 2, selected from any one of

4-[(4-benzyl-1-piperazinyl)(8-quinolinyl)methyl]-N,N-diethylbenzamide dihydrochloride (compound 2);

N,N-diethyl-4-[[4-(4-methylbenzyl)-1-piperazinyl](8-quinolinyl)methyl]benzamide (compound 5);

4-[{4-[4-(tert-butyl)benzyl]-1-piperazinyl}(8-quinolinyl)methyl]-N,N-diethylbenzamide dihydrochloride (compound 8);

N,N-diethyl-4-[[4-(4-nitrobenzyl)-1-piperazinyl])(8-quinolinyl)methyl]benzamide dihydrochloride (compound 9);

4-[{4-[2,4-bis(trifluoromethyl)benzyl]-1-piperazinyl}(8-quinolinyl)methyl]-N,N-diethylbenzamide dihydrochloride (compound 10);

N,N-diethyl-4-[[4-(4-methoxybenzyl)-1-piperazinyl](8-quinolinyl)methyl]benzamide dihydrochloride (compound 11);

4-[[4[2,4-dichlorobenzyl)-1-piperazinyl](8-quinolinyl)methyl]-N,N-diethylbenzamide dihydrochloride (compound 12);

N,N-diethyl-4-[[4-(2-pyridinylmethyl)-1-piperazinyl](8-quinolinyl)methyl]benzamide dihydrochloride (compound 13);

N,N-diethyl-4-[[4-(3-thienylmethyl)-1-piperazinyl](8-quinolinyl)methyl]benzamide (compound 14);

N,N-diethyl-4-[[4-(2-furanylmethyl)-1-piperazinyl](8-quinolinyl)methyl]benzamide (compound 15);

N,N-diethyl-4-[[4-(3-furanylmethyl)-1-piperazinyl](8-quinolinyl)methyl]benzamide (compound 16);

N,N-diethyl-4-[[4-(2-thiophenylmethyl)-1-piperazinyl](8-quinolinyl)methyl]benzamide dihydrochloride (compound 17);

N,N-diethyl-4-[[4-(2-imidazolylmethyl)-1-piperazinyl](8-quinolinyl)methyl]benzamide dihydrochloride (compound 18);

N,N-diethyl-4-[[4-(4-imidazolylmethyl)-1-piperazinyl](8-quinolinyl)methyl]benzamide dihydrochloride (compound 19); and N,N-diethyl-4-[4-(3-triazolylmethyl)-1-piperazinyl](8-quinolinyl)methyl]benzamide dihydrochloride (compound 20).

4. A compound according to any one of claims 1–3, which compound is present as the (+)-enantiomer.

5. A compound according to any one of claims 1–3, which compound is present as the (−)-enantiomer.

6. A compound according to any of the preceding claims, in form of its hydrochloride, sulfate, tartrate or citrate salts.

7. A compound selected from the group consisting of:
(+)4-[(4-benzyl-1-piperazinyl)(8-quinolinyl)methyl]-N,N-diethylbenzamide; and
(+)4-[[4-(4-methylbenzyl)-1-piperazinyl](8-quinolinyl)methyl]-N,N-diethylbenzamide.

8. A compound selected from the group consisting of:
(−)4-[(4-benzyl-1-piperazinyl)(8-quinolinyl)methyl]-N,N-diethylbenzamide; and
(−)4-[[4-(4-methylbenzyl)-1-piperazinyl](8-quinolinyl)methyl]-N,N-diethylbenzamide.

9. A pharmaceutical composition comprising a compound of the formula I according to claim 1 as an active ingredient, together with a pharmacologically and pharmaceutically acceptable carrier.

10. A method for the treatment of pain, whereby an effective amount of a compound of the formula I according to claim 1 is administered to a subject in need of pain management.

11. The compound of claim 1, wherein $R^1$ is phenyl.

12. The compound of claim 1, wherein $R^1$ is pyridinyl.

13. The compound of claim 1, wherein $R^1$ is thiophenyl.

14. The compound of claim 1, wherein $R^1$ is furanyl.

15. The compound of claim 1, wherein $R^1$ is imidazolyl.

16. The compound of claim 1, wherein $R^1$ is triazolyl.

17. The compound of any one of claims 11–16, wherein said compound is present as the (+)-enantiomer.

18. A pharmaceutical composition comprising a compound according to claim 17 as an active ingredient, together with a pharmacologically and pharmaceutically acceptable carrier.

19. A method for treating a subject for pain, comprising administering to said subject an effective amount of the compound of claim 17.

20. The compound of any one of claims 11–16, wherein said compound is present as the (−)-enantiomer.

21. A pharmaceutical composition comprising a compound according to claim 20 as an active ingredient, together with a pharmacologically and pharmaceutically acceptable carrier.

22. A method for treating a subject for pain, comprising administering to said subject an effective amount of the compound of claim 20.

* * * * *